United States Patent
Schmidt et al.

(10) Patent No.: US 12,383,337 B2
(45) Date of Patent: Aug. 12, 2025

(54) POSITIONING AND ORIENTATION OF A HAND-GUIDED MODALITY

(71) Applicant: Siemens Healthineers AG, Forchheim (DE)

(72) Inventors: Oliver Schmidt, Erlangen (DE); Sabine Mollus, Jülich (DE); Oliver Hornung, Unterleinleiter (DE); Amilcar Alzaga, Schönbrunn im Steigerwald (DE); Jens-Christoph Georgi, Oberasbach (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/976,599

(22) Filed: Dec. 11, 2024

(65) Prior Publication Data

US 2025/0195145 A1 Jun. 19, 2025

(30) Foreign Application Priority Data

Dec. 14, 2023 (DE) ...................... 10 2023 212 746.6

(51) Int. Cl.
| | |
|---|---|
| A61B 34/00 | (2016.01) |
| A61B 5/00 | (2006.01) |
| A61B 5/055 | (2006.01) |
| A61B 6/00 | (2006.01) |
| A61B 6/03 | (2006.01) |
| A61B 8/00 | (2006.01) |

(Continued)

(52) U.S. Cl.
CPC ............ *A61B 34/10* (2016.02); *A61B 5/0035* (2013.01); *A61B 5/055* (2013.01); *A61B 6/032* (2013.01); *A61B 6/037* (2013.01); *A61B 6/5247* (2013.01); *A61B 8/0841* (2013.01); *A61B 8/5261* (2013.01); *A61B 18/1477* (2013.01); *A61B 2018/00577* (2013.01); *A61B 2018/00982* (2013.01); *A61B 2034/104* (2016.02); *A61B 2034/107* (2016.02)

(58) Field of Classification Search
CPC ....................................................... A61B 34/10
See application file for complete search history.

(56) References Cited

U.S. PATENT DOCUMENTS

2013/0035583 A1 2/2013 Park

FOREIGN PATENT DOCUMENTS

WO 2006036458 A1 4/2006

OTHER PUBLICATIONS

German Office Action for App. No. 10 2023 212 746.6 mailed on Aug. 7, 2024, with English translation.

*Primary Examiner* — Joseph M Santos Rodriguez
(74) *Attorney, Agent, or Firm* — Lempia Summerfield Katz LLC

(57) ABSTRACT

A hand-guided modality is to be positioned with little effort or radiation load. To this end an object model is created from 3D data of an object. Moreover, a surface model of the object is created. Both models are registered to one another. Depending on a target region in the object model, a start position and a start orientation of the hand-guided modality are calculated. Moreover, a target image of the object is calculated on the basis of the object model, the target region and also the start position and start orientation. A real ultrasound image is further acquired from the start position and start orientation. A repositioning and/or re-orientation of the hand-guided modality is undertaken on the basis of a deviation between the ultrasound image and the target image.

20 Claims, 3 Drawing Sheets

(51) Int. Cl.
*A61B 8/08* (2006.01)
*A61B 18/14* (2006.01)
*A61B 34/10* (2016.01)
*A61B 18/00* (2006.01)

POSITIONING AND ORIENTATION OF A HAND-GUIDED MODALITY

CROSS REFERENCE TO RELATED APPLICATIONS

This application claims the benefit DE 10 2023 212 746.6 filed on Dec. 14, 2023, which is hereby incorporated by reference in its entirety.

FIELD

Embodiments relate to a method for positioning and orienting a hand-guided modality.

BACKGROUND

Microwave and high-frequency ablation is an option for therapy in early stages of liver cancer. An ablation needle must be positioned precisely in the tumor that is to be ablated. As a rule, a pre-interventional 3D imaging study (CT or MR) that depicts the location of the tumor is available. For the intervention it is essential to introduce the needle and to place it in the optimum way. To do this, the doctor may be assisted by imaging methods.

There are various methods for controlling the positioning of the needle. Ultrasound is used as a real-time imaging system for example in order to visualize the needle during its introduction. In a few cases the pre-interventional MR or CT datasets are registered with the live ultrasound signal in order to assist in localizing the tumor. The registration may be rigid or elastic. The visualization may be undertaken by images arranged next to one another or by superimposed images. For a robust registration a tracking device is required as a rule, that continuously monitors the position and alignment (or orientation) of the ultrasound probe and adjusts the visualization of the CT/MR dataset accordingly. The registration is initiated by the identification of landmarks (striking features in the image, for example vessels) both in ultrasound and also in CT/MR either by user interaction or by automatic image analysis. As a rule, at least two image planes from different directions are needed in order to localize such landmarks in 3D. As an alternative a 3D sweep (recording rows from at least two different directions) with ultrasound may be carried out and the number of image stacks may be aligned with one another either by manual user interaction or by a suitable algorithm. In general, the image registration, because of the deformation or the organs as a result of changes in the positioning of the patient and breathing artifacts, is complicated and requires trained and experienced operators to enable these methods to be carried out.

In more advanced practices CT or MR devices are used for constant monitoring of the positioning of the needle. The advantage of this approach is that a complete 3D dataset is available, that makes the positioning of the needle easier. The disadvantage is that CT (Computed Tomography) is associated with a radiation load for patients and operators and MR (Magnetic Resonance Tomography) is associated with restricted accessibility and high costs.

BRIEF SUMMARY AND DESCRIPTION

This scope of the present disclosure is defined solely by the claims and is not affected to any degree by the statements within this summary. The present embodiments may obviate one or more of the drawbacks or limitations in the related art. Independent of the grammatical term usage, individuals with male, female or other gender identities are included within the term.

Embodiments provide precise imaging for the intervention as an alternative to CT and MR.

A method is provided for positioning and orientation of a hand-guided modality. In the whole of the present document the term "ultrasound facility" is also used to represent other hand-guided modalities (for example a SPECT device; Single Photon Emission Computed Tomography). The term "hand-guided" means that at least a part of the modality (for example the probe) is able to be guided by hand. The ultrasound facility is to be employed as an alternative to the burdensome CT methods and expensive MR methods. In order however to achieve a high image quality, for example for the positioning of (medical) instruments, it is necessary to position and to orient the ultrasound facility very precisely. As well as its position, its alignment is also of decisive importance for the ultrasound facility.

In one step of the method, 3D data of an object is loaded. The loading of the data may be part of an acquisition process. The 3D data (for example MR or CT data) may however also be provided from a memory medium or via an interface. In this case they are to be loaded or to be stored in a working memory of a processing device. An object may involve a human or animal patient, but may also involve a technical object.

In a further step, an object model of the object is automatically created from the 3D data. The object model as a rule involves a 3D model that reproduces the object with its internal structure. The object model may also for example include corresponding segmented spatial regions. In the case of a patient the object model involves a patient model, that preferably reproduces important internal organs, such as liver, vessels, rib cage etc. The object model may be obtained automatically by a suitable application from the 3D data.

In the method, a target region in the object model is specified as well. This target region may for example be a lesion that is to be observed or treated. This target region is for example marked automatically by user interaction in the object model. Where necessary the target region may also be established automatically or may be specified by entering data.

Furthermore, surface data of the object is acquired. Since the ultrasound facility must be placed on the surface of the object it is essential to acquire the surface of the object at least partly. The acquisition is undertaken for example optically or where necessary with other electromagnetic techniques, when for example markers are available on the surface. The acquisition technique should be tailored to the surface properties of the object.

A surface model of the object is automatically created from the surface data. Independently of the object model, a surface model of the object or patient is thus generated automatically. While the object model is created automatically from complex, for example 3D data (for example MR or CT) obtained pre-interventionally, a current surface model may easily be obtained from data obtained optically.

Where necessary a first-surface model is additionally also already acquired pre-interventionally during the recording of the object model. The direct link between object and surface model is then available there and may be synchronized with the new or current surface model during the ultrasound-assisted intervention.

This for example includes the advantage that the two surface models may contain a larger section of the patient than the object model and thus makes the registration easier.

In a further step, the surface model is registered with the object model. The object model likewise reproduces a surface structure, that is synchronized or registered with that of the surface model. This makes it possible to estimate the internal structure of the object in relation to the position and orientation with the aid of a current surface model. Under some circumstances the above-mentioned first-surface model may be used for the registration.

Furthermore, a start position and start orientation of the ultrasound facility on the object model are calculated automatically as a function of the target region. The ultrasound facility and for example its probe must be placed on the object. The start position and start orientation of the ultrasound facility as a function of the desired target region on the object model are calculated virtually in order to do this. Since the surface model is registered with the object model, an updated object model is more or less available, on the surface of which the ultrasound facility is to be placed and oriented virtually. Thus, a first estimation for position and orientation of the ultrasound facility is obtained, in order to obtain suitable recordings from the target region.

In a further step, a target image from a part area of the object is automatically calculated on the basis of the object model, the target region and also the start position and start orientation of the ultrasound facility. From the start position and start orientation of the ultrasound facility a target image (for example a virtual ultrasound image) is thus estimated, that reproduces a part area of the object. To do this, a slice representation (the target image) is calculated from the 3D dataset, that corresponds to the start position and orientation. It is the user's responsibility to adapt the real ultrasound image so that it matches the calculated target image. In this case the user, thus starting from a calculated MR/CT contrast image, that was calculated for a corresponding slice from the 3D or voxel dataset, may undertake the comparison with the real ultrasound image. The part region of the object mentioned preferably includes the above-mentioned target region (ROI: Region of Interest). Since the recording geometry of the ultrasound facility is known as a rule, the target image is able to be estimated with the aid of the established start position and start orientation of the ultrasound facility with the help of the object model. In the present document the term "virtual ultrasound image" is also used as representative of the term "target image". As well as the ultrasound image (simulated US contrast image) the calculated target image may also involve a CT contrast image or MR contrast image.

Furthermore, in the method a real ultrasound image of the part region of the object is acquired by the ultrasound facility in the start position and start orientation. To do this, the real ultrasound facility is brought into the real start position and real start orientation, that correspond to the virtual start position and virtual start orientation that have been calculated automatically. Where necessary the virtual data corresponds to real data, wherein the data may be identical or may be obtained by coordinate transformation.

In a subsequent step, the (real) ultrasound facility is repositioned and/or reorientated on the basis of a deviation between the target image and the real ultrasound image. This repositioning or reorientation may be undertaken automatically, partly automatically or manually. The deviation between the target image and the real ultrasound image may be established for example with the aid of a landmark. If, for example, a vessel branch in the target image lies in a different image region from that which it lies in the real ultrasound image, then a corresponding deviation is present, that may be corrected where necessary with a re-orientation of the real ultrasound facility (completely or in large part). With the target image, that is acquired on the basis of the object model or of the preferably pre-interventionally acquired 3D data, the real ultrasound facility may thus be optimally positioned and orientated, since the object model is updated with the easy-to-obtain surface model. Thus, an ultrasound facility may easily be (optimally) positioned and oriented without additional radiation load.

Thus, the user may be helped to identify landmarks, lesions/tumors and needles with greater certainty and to accelerate the respective workflow. In the method, information about the inside of the body (3D MR/CT data), information about the body surface (patient avatar based on sensor data such as from a stereoscopic camera) and information about the actual position/alignment of the ultrasound probe may be used in order to establish the suitable target position/alignment of the ultrasound probe for visualization of landmarks, lesions and needles (device).

In an embodiment there is provision for the object to be a patient, and, in the automatic creation of the object model, for organs of the patient to be automatically segmented. The object model thus involves a patient model, in which organs such as the liver, vessels or the like are modeled separately. The modeling is based on the 3D data. Where necessary the patient model may be supplemented by a deformation model, in order for example to take account of deformations that are produced by patient positionings and breath artifacts.

In accordance with a further embodiment the target image is a calculated ultrasound image, MR image or CT image. Thus, the virtual image may be created in such a way that is optimal for the respective situation.

In another embodiment there is provision, in addition to the 3D data of the object, for first-surface data of the object that is obtained during an acquisition of the 3D data, also to be loaded, for a first-surface model to be created from the first-surface data, and for the first-surface model, that is implicitly registered with the object model, to be used for registration of the surface model with the object model. This has the advantage that a first-surface model of the object may be obtained pre-interventionally in the same situation as the 3D data or the object model of the object. The first-surface model is thus automatically registered with the object model and may thus be used for an indirect registration of the object model with the current surface model.

In a further embodiment, a 3D-camera is used for the acquisition of the surface data of the object, with which a position and orientation of the hand-guided modality is also acquired. Thus the 3D-camera is given a double functionality.

There may further be provision in an embodiment for a position and orientation of an instrument that is optionally guided on the hand-guided modality to be acquired with the 3D camera. Thus the 3D-camera is given a further functionality, namely the monitoring of the instrument. Here, by way of example, the procedure is as follows: The needle (i.e. the instrument) is pushed forwards through a guide rail attached to the ultrasound head, or the operator guides the ultrasound head with one hand and the needle holder with the other hand.

In a further embodiment, a path of an instrument in the part region of the object is planned with the aid of the object model, and the path is included for the automatic calculation of the target image (for example virtual ultrasound image).

The instrument may for example involve a treatment instrument such as for example an ablation needle. The path of an ablation needle or the like may for example be planned with a treatment model. In this case, inter alia, hidden structures such a ribs may be taken into account. Thus, for example the path must be planned to go past the ribs. The planned path may be used to calculate the virtual ultrasound image. In the ultrasound image the path should be easily visible (in-plane). Consequently, the planned path should be taken into account for the optimization of the position and orientation of the ultrasound facility.

The planning of the path may include a repositioning of the object. For example, if in a first planning step a first path outline is planned that does not prove to be optimal for the treatment. Therefore, the further planning may include the step of the object or the patient being repositioned. This means that the pose (position and orientation) of the object is changed. Through this as a rule not only does the spatial relationship of part structures of the object to external apparatuses (treatment instruments, ultrasound facility and the like) change, but where necessary also changed deformations of the inner structures or organs of the object/patient.

In a further embodiment there may be provision for the repositioning of the object to be taken into account by an updating of the object model by a deformation model. As has already been indicated above, the object model may be supplemented by a deformation model, in order to take into account current deformations (for example of organs of a patient) for the path planning of an instrument or the positioning and orientation of an ultrasound facility. For example, in this way for example a surface deformation in the 3D object model that is registered on the surface model may be extrapolated.

In a further embodiment, with the automatic calculation of the virtual ultrasound image, an acquisition geometry of the ultrasound facility may be taken into account. For the acquisition geometry, as well as the position and orientation of the ultrasound facility, the opening angle for the imaging may also be counted for example. If for example a previously known ultrasound facility is used then it is advantageous for the virtual ultrasound image to adapt the acquisition geometry to the real ultrasound facility. This enables the similarity of virtual and real ultrasound images to be increased. The acquisition geometry may also include the respective selected plane of an ultrasound image acquisition in relation to an instrument (for example cannula or needle).

In a specific embodiment, in the automatic calculation of the virtual ultrasound image, an optimization in relation to various ultrasound image planes is carried out. For example, so-called in-plane ultrasound images or off-plane (out-of-plane) images may be acquired. With the in-plane technique for example the cannula or needle runs in the sound plane. In the off-plane technique the cannula or needle intersects with the sound plane. In the latter case for example sound head and needle are at an angle of for example 90 degrees to one another. Where necessary a user may also contribute to the optimization of the virtual ultrasound image in relation to the respective plane and may define the plane with a suitable interface.

In a further embodiment there may be provision for a user interaction to be taken into account for the repositioning and/or reorientation of the ultrasound facility. In this way for example it is advantageous to provide an interface for a so-called fine tuning, that makes it possible for the user to at least partly reposition or re-orientate the ultrasound facility. Thus, for example, for a fine tuning, the repositioning or reorientation may also be carried out manually or partly automatically.

In another embodiment, the deviation between the virtual ultrasound image and the real ultrasound image is determined for the repositioning and/or reorientation of the ultrasound facility with just a single landmark in both ultrasound images. For example, a single vessel branch is used as a landmark for recognizing a deviation between the real and virtual ultrasound image and for registering the two images with each other accordingly. A number of landmarks may then be observed in a fine-tuned registration.

In this way a first rough repositioning may be undertaken with the aid of a single landmark, while a further fine positioning is carried out by a number of landmarks.

In the course of an optimization of the position or orientation of the ultrasound facility, in one embodiment there may be provision for the steps of acquiring a real ultrasound image and also the repositioning and/or reorientation of the ultrasound facility to be repeated a number of times alternately in order to minimize a difference between virtual and real ultrasound image. Thus, in an optimization loop, after each repositioning or re-orientation, an ultrasound recording may be made in order to compare the recording once again with the virtual ultrasound image.

In an embodiment, a path for an instrument is determined mechanically by the positioning and orientation of the ultrasound facility. For example, the ultrasound facility possesses a guide element (for example a guide rail) on its housing. Thus, with the positioning and orientation of the ultrasound facility the path for the instrument is also positioned and orientated. This enables the path for the instrument to be determined in a simple way at the same time with the ultrasound facility. As an alternative or in addition, as mentioned above, via a 3D camera or stereoscopic camera, with which the surface data of the object is also acquired where necessary, the position and orientation of the instrument/needle may likewise be monitored and controlled.

The above-mentioned object is also achieved by an apparatus with a hand-guided modality, a first acquisition facility for loading (where necessary acquiring) 3D data (MR, CT) of an object and also for specifying a target region (for example lesion) in the object model, a second acquisition facility for acquisition of surface data of the object, a computing facility configured for automatic creation of an object model of the object from the 3D data, automatic creation of a surface model of the object from the surface data, registration of the surface model with the object model, automatic calculation of a start position and start orientation of the hand-guided modality on the object model on the basis of the target region, and automatic calculation of a target image of a part region of the object (ROI) on the basis of the object model, the target region as well as the start position and start orientation of the hand-guided modality, wherein a real ultrasound image of the part region of the object is able to be acquired by the ultrasound facility in the start position and start orientation with the hand-guided modality and the apparatus includes a display facility, configured for visualizing a deviation between the target image and the real ultrasound image.

On the basis of the deviation between the target image and the real ultrasound image, the hand-guided modality may be repositioned and/or reoriented (automatically/manually). In this case the positioning and orientation of the hand-guided modality means that at least a part of the hand-guided modality (for example ultrasound probe) is positioned or orientated.

The ultrasound facility is an imaging facility based on ultrasound. It may include an ultrasound probe, that is typically placed on the surface of the object or of the patient for ultrasound recordings.

The first acquisition facility is configured at least to load 3D data of the object. Thus, this 3D data may for example be provided by a memory unit. For example, in this way pre-interventional data may be made available for the apparatus. Where necessary the first acquisition facility may also include an MR or CT scanner, with which the 3D data is recorded and provided directly. Furthermore, the first acquisition facility is also configured to specify the target region in the object model. This may be undertaken by target data being loaded once again. As an alternative the specification of the target region may be undertaken by user interactions being accepted via a corresponding interface and target region coordinates being converted. In this way for example a user may mark a lesion in a three-dimensional object model, whereby the target region is determined.

The second acquisition facility for acquisition of the surface data may for example include a stereoscopic camera, with which the surface of the object is acquired optically.

The computing facility for creating the object model and the surface model and also for registration of the two models, but also for calculation of the start position and start orientation of the ultrasound facility and for calculation of the target image may include a computer or processor with memory elements. The computing facility may however under some circumstances also handle control tasks for control of the ultrasound facility and the acquisition facilities.

The positioning facility of the apparatus may include positioning functionality for automatic, semi-automatic or manual positioning and/or orientation. This enables the ultrasound facility or a part thereof to be positioned and aligned in respect of the target region.

For the apparatus the same advantages and variation options apply by analogy as for the method illustrated above and vice versa. The features of the method may therefore be seen as corresponding functional features of the apparatus.

In an embodiment, the ultrasound facility includes a needle guide for guiding an ablation needle or a cannula. The needle guide may be configured as a mechanical guide, that makes a degree of freedom of movement possible for the ablation needle or the cannula for example. Where necessary the corresponding instrument (for example ablation needle or cannula) may be moved automatically by a drive mechanism in the needle guide. The needle guide may be attached permanently to the ultrasound facility and for example to a housing of the ultrasound facility. This has the advantage that, with the alignment or positioning of the ultrasound facility, the needle guide is also positioned and aligned automatically.

In a further embodiment, the apparatus furthermore includes a planning facility, in order to plan a path of an instrument in the part region of the object with the aid of the object model, and also a navigation facility for navigating the instrument along the planned path as a function of a real ultrasound image that is recorded after the repositioning and/or reorientation of the ultrasound facility. The planning facility and/or the navigation facility may be based on a processor or computer. The planning facility may include a corresponding HMI interface. Via the HMI interface for example the required and the actual position of the ultrasound probe and/or of the instrument may be displayed, in order to give the user information for changing the actual position. The navigation facility may include corresponding control elements, in order activate a separate drive facility for the ultrasound facility or the ultrasound facility itself.

For application cases or application situations that may arise in the method and that are not described explicitly here, there may be provision, in accordance with the method, for an error message and/or a request to enter a user acknowledgement to be output and/or for a default setting and/or a predetermined initial state to be set.

Independent of the grammatical term usage, individuals with male, female or other gender identities are included within the term.

DETAILED DESCRIPTION

Figure 1:
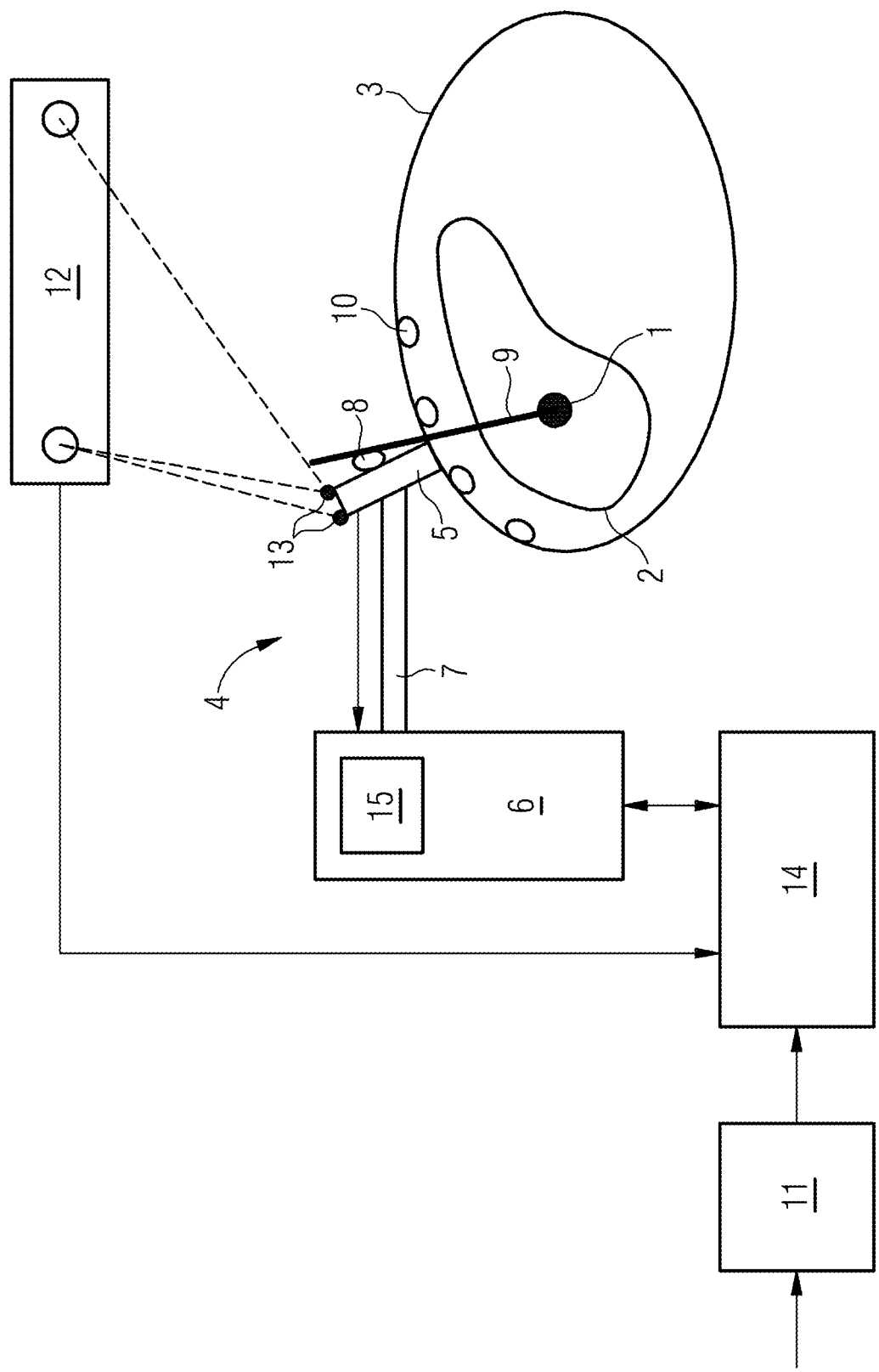
FIG. 1 depicts a schematic view of an embodiment of an apparatus.

The apparatus shown in FIG. 1 may be understood as a system for assisting a user during the positioning of an ultrasound probe, so that the registration process and a possible needle positioning may be facilitated. For example, the apparatus is to be used for a system with which a liver tumor 1 in a liver 2 of a patient 3 may be treated. The patient 3 here represents the object for the ultrasound examination or the treatment. The ultrasound facility 4 in the present example possesses an ultrasound probe 5, an evaluation and control unit 6 and optionally a positioning facility 7. Preferably the ultrasound probe 5 is hand guided and where necessary there is monitoring of the position and orientation by a second acquisition facility (for example a stereoscopic camera). Via the positioning faculty 7 the ultrasound probe 5 may be positioned and orientated from the evaluation and control unit 6, for example on the surface of the object or patient 3.

The ultrasound facility may for example involve a 2D ultrasound system. It may for example deliver real-time b-mode images.

The ultrasound probe 5 may include a guide 8 with which for example an ablation needle 9 may be guided from outside through the rib cage and the liver 2 of the patient 3. It should be ensured in this case for example that the path of the ablation needle 9 does not intersect with a rib 10.

In the present case the liver tumor 1 or a part thereof would be the target region, that on the one hand is to be reached by the ablation needle 9 and that on the other hand is to be imaged by the ultrasound facility 4. For example, it is of advantage in this case for the ultrasound facility 4 to be capable of real time imaging of the target region.

The apparatus of FIG. 1 also includes a first acquisition facility 11 for loading of 3D data of the patient 3. For example, in this way a 3D dataset of the patient 3 obtained pre-interventionally may be used for the apparatus. The 3D dataset may for example originate from an MR or CT system. For example, the dataset should represent the target region. The acquisition facility 11 may include an interface to the Internet, a CD or DVD drive or another data interface. Where necessary the first acquisition facility 11 is however also part of an MR or CT system or the like. In the present example the 3D dataset may originate from an MRT examination of a liver, wherein segmented lesions are provided for an ablation.

The apparatus shown in FIG. 1 includes a second acquisition facility 12 for acquisition of surface data of the object or patient 3. In the present example it may involve a stereoscopic camera, with which the surface of the patient 3 is able to be scanned in three dimensions. Thus, an avatar of the surface of the patient (surface model) may be formed and, together with the 3D data, the internal position of the liver estimated. The stereoscopic camera may already acquire a surface model of the patient during the pre-interventional image acquisition and make it available together with the object model via acquisition facility 11. Where necessary the surface model, that is acquired during the pre-interventional image acquisition, may be used in order to calculate the registration with the interventional surface model and the virtual surface model. As an option, visible markers may be placed on the patient's body during the pre-interventional image acquisition. Where necessary the markers may be used again during the intervention.

The ultrasound probe 5 may also include one or more markers 13, by which the second acquisition facility 12 may recognize the position and/or orientation of the ultrasound probe 5. This enables the second acquisition facility 12 to make available not only data of the patient 3 but also position and orientation data of the ultrasound probe 5 for the control of the apparatus.

Furthermore, the apparatus shown in FIG. 1 possesses a computing facility 14. The computing facility 14 may serve for example to automatically create the patient model from the 3D data. Moreover, it may be used for creation of the surface model of the patient 3 from that data of the second acquisition facility 12. It may further also be useful for estimating a suitable position and orientation in order to place the ultrasound facility 4 or its ultrasound probe 5 so that the target region (ROI) is visible. To this end the computing facility 14 may for example automatically calculate a start position and start orientation of the ultrasound facility 4 on the object model or surface model, so that the target region is visible. The start position and start orientation thus represent a rough pose of the ultrasound facility 4.

The computing facility 14 may serve to calculate a virtual ultrasound image of the part region of the object as a function of the object model, to automatically calculate the target region and also the (start) position and (start) orientation of the ultrasound facility 4. Thus, for example virtual b-mode ultrasound images are simulated on the basis of the 3D datasets, wherein the anatomy of the patient 3 is taken into account. That image may be sought from the virtual ultrasound images or target images in which the target region is best visible.

Thus, while a virtual ultrasound image is calculated with the computing facility 14, a real ultrasound image of a part region of the patient 3 may be obtained with the ultrasound facility 4. A deviation between the virtual ultrasound image or target image and the real ultrasound image may be used to reposition or to reorientate the ultrasound facility 4. The computing facility 14 may in its turn establish this deviation between the two ultrasound images. To do this, the computing facility 14 for example uses a single or also a number of landmarks in the two ultrasound images. An optimum position and orientation of the ultrasound facility 4 may be produced when the deviation is minimal or the two ultrasound images match.

The apparatus may include a feedback device that helps the user to place the ultrasound probe. For example, this feedback device may be a monitor (not shown in FIG. 1), that depicts the planned and current position of the ultrasound probe 5 and where necessary also gives instructions as to where it is to be moved to. As an alternative a laser guidance system may also be used, that specifies an optimal location and an optimal orientation.

A monitor 15 (the same or a different monitor) may be provided, that reproduces the real time ultrasound images and the virtual ultrasound images and thereby gives the user an opportunity to adapt the real ultrasound image until such time as it matches the virtual image (target image). Optionally the views may be shown alongside one another or overlaid with the 3D data.

The apparatus shown in FIG. 1 for positioning and orientation of the ultrasound facility 4 may also be used to position and/or to orient an instrument, such as for example the ablation needle 9. This means that the second acquisition facility 12, the computing facility 14 and the feedback device may be used for this purpose.

Figure 2:
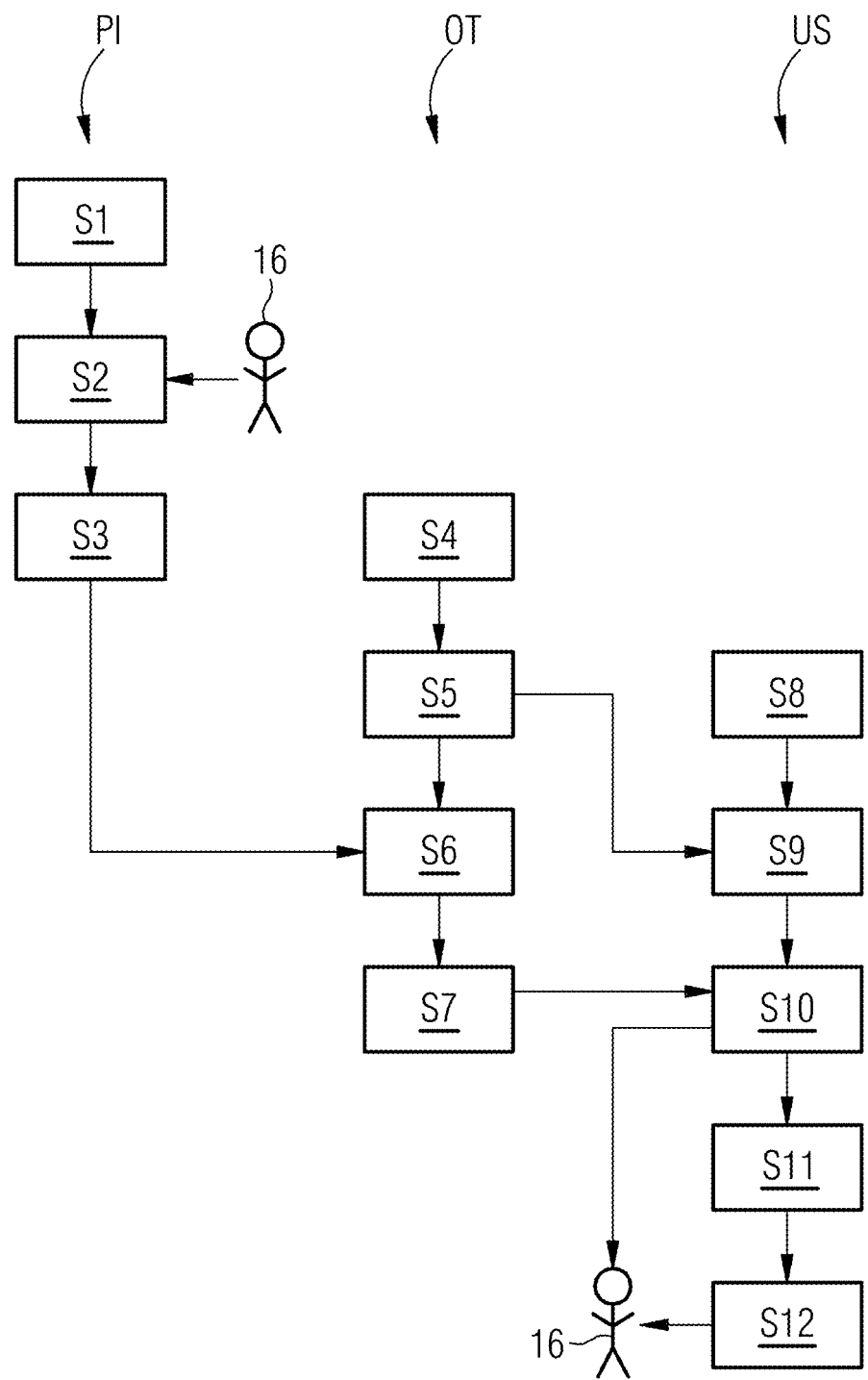
FIG. 2 depicts a schematic flow diagram of an embodiment of a method.

An example system may be based on a 3D MR/CT imaging system for pre-interventional imaging, an optical tracking system and an ultrasound device for the real time imaging ("live"). An application sequence for this is shown schematically in FIG. 2. In a pre-interventional stage PI, in a step S1 3D data (for example MR or CT data) is acquired from the region of interest. This region of interest for example covers the abdominal body region including the liver. A surface model may also be acquired or markers may also be placed on the body surface. In step S1 a patient model is also created from the 3D dataset. To do this, the surface of the patient, the rib cage, the objects of interest such as the surface of the liver, the liver vessels and the bile ducts as well as the target lesion(s) are segmented with the help of known automatic and user-guided segmentation methods.

In a step S2 the target region or the target lesion is marked, for example by a user 16, in the 3D object model. There may also be a modeling of the treatment. With special visualization and interaction tools the user 16 may for example plan the best path for the placing of the treatment devices (needles, cannulas etc.) in relation to the target lesion, structures at risk and concealing structures (such as the chest). As an additional function the repositioning of the patient 3 for better access to the treatment location could be modeled with the help of specific body deformation modeling and shaping techniques.

As step S3 the extraction of the surface of the patient is highlighted here separately once again. In the simplest case the surface of the patient corresponds to the surface of the patient segmented in step S1. Where necessary however any deformations in accordance with step S2 are also be taken into account in this case.

In an optical tracking stage OT in a step S4 there is the initialization of a navigation system for a surface-based registration. For example, a multi-stage registration may be required in order to roughly align the patient and the treatment model to the imaging ultrasound system that is used for the image-based live treatment guidance. The patient 3 is positioned in the planning step as previously described.

In accordance with step S5 the navigation system (second acquisition facility 12) "scans" the surface of the patient 3 and creates a live-surface model (avatar) of the patient's body including the markings placed on the body.

In step S6 the body surface of the live image and the body surface of the pre-interventional patient model obtained according to step S3 are reconciled with one another or registered to one another. If necessary, the patient model is deformed with the help of specific deformation models. These models take the body surface (surface model)

acquired by the navigation system and also the patient model from step S1 as input and transmit the surface deformations further into deeper parts of the body, for example by 3D extrapolation and optical flow methods.

In a further step S7, as a result of the registration of the two surfaces with one another, the target lesion (target region) is calculated in relation to the avatar (surface model of the navigation system).

In an ultrasound stage US, a real time ultrasound imaging system is initialized according to step S8. In a subsequent step S9 the ultrasound probe 5 is registered in the coordinate system of the navigation system. Thus both the ultrasound system and also the optical system possess the same coordinates.

In a following step S10 an optimal probe position and probe orientation in relation to the target region (lesion) is calculated. In this case a slice representation is calculated from the 3D dataset, that corresponds to the optimal probe position and probe orientation. The representation may either be based on the type of 3D dataset (CT or MR) or optionally a virtual ultrasound image may be generated from it. The treatment path, the pre-interventional 3D dataset, the patient model including the position of the lesion, the acquisition geometry of the ultrasound system to be simulated and a model of the optimal imaging geometry of (angled) ultrasound imaging planes such as in-plane and off-plane-b-mode ultrasound images may be used as input variables for the calculation. The virtual ultrasound image may be displayed to the user 16.

In a further step S11 the probe position of the real ultrasound probe is optically tracked or acquired for example. With the second acquisition facility 12.

Figure 3:
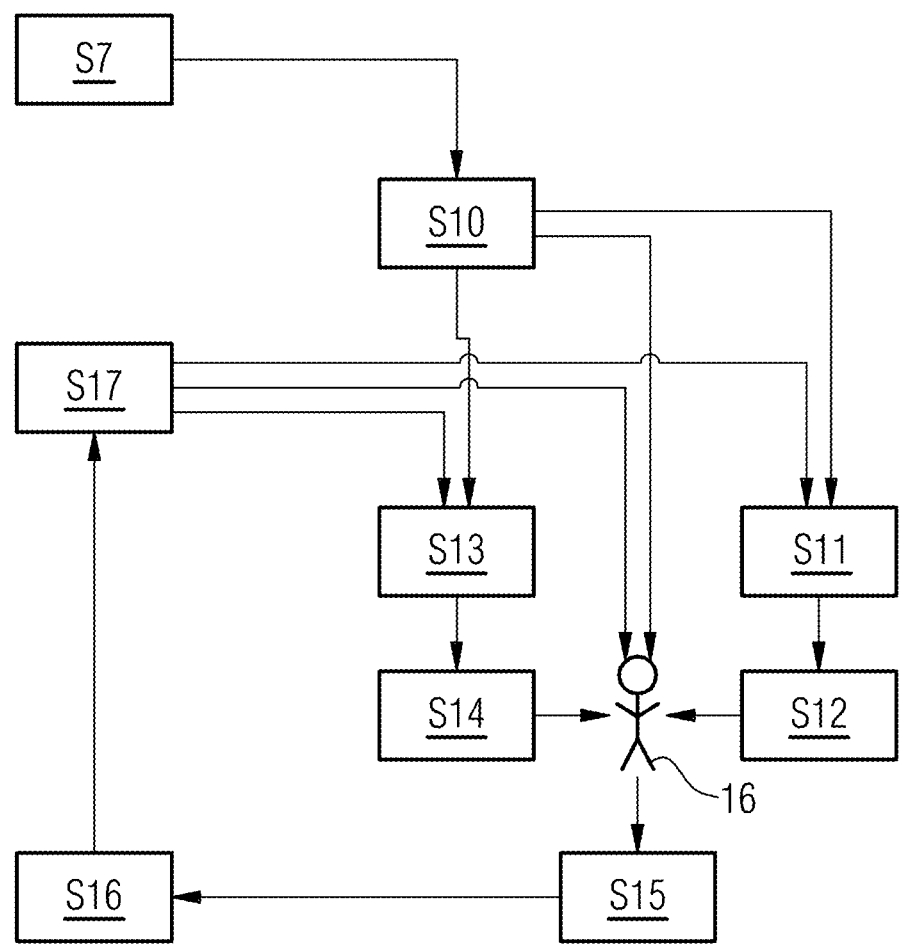
FIG. 3 depicts an actual embodiment of a method detail in a schematic execution sequence.

In step S12, the real time ultrasound image is made available to the user 16. The user may position the ultrasound probe 5 more precisely where necessary, as will be explained in more detail below in conjunction with FIG. 3. While obtaining the ultrasound image the user is asked for example to record ultrasound images, as have been planned in the virtual ultrasound imaging session. The navigation system guides the user to a corresponding probe position and orientation (start position and start orientation). To this end the navigation system (cf. FIGS. 2 and 3) establishes in step S7 the target region in relation to the avatar (surface model). Subsequently, in accordance with step S10, the optimal start position and start orientation for this are established. This start position and start orientation may be made available to the user 16. the real ultrasound facility may be provided to them, of which the probe position and orientation is tracked in accordance with step S11. The start position and start orientation in accordance with step S13 are further used, on the basis of the pre-interventional 3D dataset, to create a virtual ultrasound image. In a further step S14 the virtual ultrasound image and the real ultrasound image may be shown.

In a post-processing step the virtual ultrasound image and the real or live ultrasound image may be reconciled. This may be undertaken by the user 16 or automatically. Where necessary the user 16 or an appropriate algorithm will match the two ultrasound images to one another in accordance with step S15. Based on this matching the registration between avatar and target region is updated in accordance with step S16. With this updated registration there may be a repositioning or reorientation of the ultrasound facility 4. Thus, after the start position (first optimal position) a second optimal position and orientation may be calculated in relation to the target region in accordance with step S17. This second or refined position and orientation may be used for the steps S11 and S13 and made available to the user 16. The registration between live data stream and patient or treatment model may thus be further refined by user interaction. The refinement is undertaken for example in the loop shown in FIG. 3, that may be executed multiple times.

In a further step the navigation system may be used for a live instruction for guiding an instrument (needle, cannula etc.). In concrete terms the user, with the help of the navigation system, may be given live instructions in relation to the position of the treatment device in relation to the patient or treatment model and the live ultrasound image stream.

Thus for example the following workflow would be possible: 1) Loading a 3D imaging study, in which the target lesion has been delimited in the system. 2) Positioning of the patient on the intervention table and creation of the avatar by the system. 3) The system estimates the registration of the 3D dataset with the avatar and determines the target position/alignment of the ultrasound probe for visualization of the landmarks. 4) The user places the probe and identifies the first orientation point (landmark). 5) The system adapts the registration on the basis of the actuated measurement and proposes further positions/alignments, in order to visualize orientation points/features/lesions. 6) After conclusion of the registration the system proposes the position/alignment for the positioning of the needle and depicts the ideal trajectory of the needle in the live image and in the registered image. 7) The introduction of the needle is either assisted by a physical needle holder attached to the ultrasound probe or may be guided by the navigation/tracking system. 8) When the needle is optimally positioned in the first ultrasound pose, the system proposes a second position/alignment in order to confirm the needle positioning in 3D.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for positioning and orientating a hand-guided modality, the method comprising:
    loading 3D data of an object;
    creating an object model of the object from the 3D data;
    specifying a target region in the object model;
    acquiring surface data of the object;
    creating a surface model of the object from the surface data;
    registration of the surface model with the object model,
    calculating a start position and start orientation of the hand-guided modality on the object model as a function of the target region;

calculating a target image from a part region of the object based on the object model, the target region, and the start position and start orientation of the hand-guided modality;

acquiring a real ultrasound image from the part region of the object by the hand-guided modality in the start position and start orientation; and repositioning and/or reorientating of the hand-guided modality based on a deviation between the virtual ultrasound image and the real ultrasound image, where the target image is the virtual ultrasound image.

2. The method of claim 1, wherein the object is a patient and, in the creating of the object model, organs of the patient are segmented.

3. The method of claim 1, wherein the target image is a calculated ultrasound image, MR image, or CT image.

4. The method of claim 1, wherein, in addition to the 3D data of the object, first-surface data of the object, that is obtained during an acquisition of the 3D data, is loaded, wherein a first-surface model is created from the first-surface data, and the first-surface model that is registered implicitly with the object model, is used for registration of the surface model to the object model.

5. The method of claim 1, wherein a 3D camera is used for the acquisition of the surface data of the object, with which a position and orientation of the hand-guided modality is also acquired.

6. The method of claim 5, wherein a position and orientation of an instrument is acquired with the 3D camera.

7. The method of claim 1, wherein a path of an instrument in the part region of the object is planned with the aid of the object model, and the path is included for the calculation of the target images.

8. The method of claim 7, wherein the planning of the path comprises a repositioning of the object.

9. The method of claim 8, wherein the repositioning of the object is taken into account by an updating of the object model by a deformation model.

10. The method of claim 1, wherein, in the calculation of the target image, an acquisition geometry of the hand-guided modality is taken into account.

11. The method of claim 10, wherein, in the calculation of the target image, an optimization in relation to the various ultrasound image planes is carried out.

12. The method of claim 1, wherein a user interaction is taken into account for the repositioning and/or reorientation of the hand-guided modality.

13. The method of claim 1, wherein the deviation between the virtual ultrasound image and the real ultrasound image is determined for the repositioning and/or reorientation of the hand-guided modality with just a single landmark in both ultrasound images.

14. The method of claim 13, wherein a further repositioning and/or reorientation of the hand-guided modality with at least one further landmark is undertaken in both ultrasound images.

15. The method of claim 1, wherein acquiring a real ultrasound image and repositioning and/or reorientation of the hand-guided modality are repeated alternately multiple times in order to minimize a difference between virtual and real ultrasound image.

16. The method of claim 1, wherein a path for an instrument is determined mechanically by the positioning and orientation of the hand-guided modality.

17. The method of claim 1, wherein the loading of the 3D data of the object is preceded by an acquisition of the 3D data by a modality and a simultaneous acquisition of the first-surface data of the object.

18. An apparatus comprising:
a hand-guided modality;
a first acquisition facility configured for loading of 3D data of an object and for specifying a target region in the object model;
a second acquisition facility configured for acquisition of surface data of the object;
a computing facility configured to:
creating an object model of the object from the 3D data;
creating a surface model of the object from the surface data;
registering the surface model to the object model;
calculating a start position and start orientation of the hand-guided modality to the object model on the basis of the target region; and
creating a target image of a part region of the object based on the object model, the target region, and the start position and start orientation of the hand-guided modality;
wherein a real ultrasound image of the part region of the object is acquired by the hand-guided modality in the start position and start orientation with the hand-guided modality; and
a display facility configured to visualize a deviation between the target image and the real ultrasound image.

19. The apparatus of claim 18, wherein the hand-guided modality involves an ultrasound facility or a Single Photon Emission Computed Tomography device.

20. The apparatus of claim 18, wherein the hand-guided modality includes a needle guide for guiding an instrument.

* * * * *